United States Patent [19]

Paronen et al.

[11] Patent Number: 5,667,803
[45] Date of Patent: Sep. 16, 1997

[54] STARCH ACETATE COMPOSITION WITH MODIFIABLE PROPERTIES, METHOD FOR PREPARATION AND USAGE THEREOF

[75] Inventors: Timo Petteri Paronen, Kuopio; Soili Hellevi Peltonen, Rajamaki; Arto Olavi Urtti; Leena Johanna Nakari, both of Kuopio, all of Finland

[73] Assignee: Oy Polymer Corex Kuopio Ltd., Kuopio, Finland

[21] Appl. No.: 374,430

[22] Filed: Jan. 19, 1995

[30] Foreign Application Priority Data

Jun. 7, 1994 [FI] Finland .................. 942686

[51] Int. Cl.$^6$ .................. A61K 9/20; A61K 9/46; A61K 9/24; C08B 31/02
[52] U.S. Cl. .................. 424/465; 424/464; 424/470; 424/472; 514/778; 536/102; 536/107; 536/110
[58] Field of Search .................. 424/464, 465, 424/470, 472; 514/778; 536/102, 107, 110

[56] References Cited

U.S. PATENT DOCUMENTS

| 3,622,677 | 11/1971 | Short et al. | 106/210 |
|---|---|---|---|
| 3,795,670 | 3/1974 | Mark et al. | 536/110 |
| 4,072,535 | 2/1978 | Short et al. | 106/210 |

FOREIGN PATENT DOCUMENTS

| 652281 | 8/1994 | Australia . |
|---|---|---|
| 656014 | 1/1995 | Australia . |
| 1767774 | 5/1968 | Germany . |
| 272999 | 6/1988 | Germany . |
| 1216873 | 5/1968 | United Kingdom . |
| 9301217 | 7/1991 | WIPO . |
| 9300939 | 1/1993 | WIPO . |
| 9320140 | 5/1993 | WIPO . |

OTHER PUBLICATIONS

Pradeepkumar P. et al, "Evaluation of Preflo Modified Starches as New Direct Compression Excipients.", Pharmaceutical Research, vol. 10, No. 11, (1993).

Primary Examiner—Carlos Azpuru
Attorney, Agent, or Firm—Browdy and Neimark

[57] ABSTRACT

The present invention is related to a novel type of composition with modifiable properties and suitable for controlled release of active ingredients in industrial use. The composition contains an active ingredient and starch acetate in the form of a compact. More specifically the invention relates to active ingredients such as solid dosage forms of drugs, especially compacts and tablets. In these compacts starch acetate with distinct substitution degrees are used. The starch acetate makes the process industrially feasible with good flowability and facilitates the formation of firm tablets. Starch acetate enables the controlled release of the active ingredient. The invention also discloses method for the preparation of the composition as well as its use.

51 Claims, 15 Drawing Sheets

5,667,803

STARCH ACETATE COMPOSITION WITH MODIFIABLE PROPERTIES, METHOD FOR PREPARATION AND USAGE THEREOF

THE TECHNICAL FIELD OF THE INVENTION

The present invention is related to a composition comprising starch acetate and having modifiable properties. The composition is especially suitable for use in pharmaceutical preparations, but it can also be used in fertilizers, in herbicidal preparations as well as in diagnostic preparations. The present invention also discloses a method for the preparation and the use of said composition.

THE BACKGROUND OF THE INVENTION

Pharmaceutical preparations, fertilizers, herbicidal preparations as well as diagnostic preparations typically comprise one or several excipients, in addition to the active substances, such as therapeutic substances or drugs, fertilizers, herbicides or reagents. Excipients make the manufacturing of the above mentioned products more feasible and give them suitable physicochemical, biological and biopharmaceutical properties. Excipients are used e.g. to facilitate flowability of powder mass. Other reasons are to adjust the weight uniformity and to minimize the dose variation of single dose preparations. Excipients are also used to optimize the energy consumption as well as to enhance the manufacturing rate during production.

A typical stage in the process of manufacturing solid preparations, e.g. pharmaceutical solid dosage forms, especially tablets are the compression techniques, whereby powder mass comprising the active substance/substances and excipient/excipients are densified under high pressure in order to obtain a compact with low porosity, e.g. a tablet. Because most active substances, especially drugs, are typically poorly compressable materials, they are not as such feasible for the formation of firm tablets. Thus, excipients with more favourable compressibility are added to enhance the formation of mechanically strong tablets. Commercially available excipients, for example several types of celluloses, lactoses and dicalcium phosphates can be used for said purpose in tablets.

In addition to the active substance/substances several, chemically and physically different excipients must be used in the preparations. Unfortunately, they beside making the manufacturing possible, also multiply the incompatibility risks between active substance/substances and excipients in the formulations. Incompatibilities may induce chemical and physical instability and thus shorten the shelf life of the product. This is the reason why the trend today is to use as few excipients in formulations as possible.

Granulation of powder mass is a preferred preprocess prior to compression. In a first granulation step the powder mass can be wetted either with water or with liquid binder solutions. This step is followed by a second step, which comprises aggregation of the wet and sticky powder mass. Using said procedure the particle size of the powder mass is increased. The drying process is a typical third and separate step of preprocessing. Another possible granulation method is the slugging or compaction granulation. In this process the powder mass is, firstly, compacted to form slugs, large tablets or compressed plates which are, secondly, crushed to suitable particle size for tabletting. On the other hand, using the direct compression of powder mass without granulation it is possible to accelerate and simplify the tabletting process as well as to decrease the energy consumption in manufacturing of tablets. The direct compression process is possible to perform only with free flowing, easily compactable and well compressable powder masses.

Compression of powder mass is done in a tablet press, more specifically in a steel die between two moving punches. Prior to compression, the powder mass should flow into the die. The easiness and steadiness of the flow process and thus the homogenous filling of the die determines the weight and content variation of the compressed tablets as well as the repeatability of the administered doses during drug therapy. The most important variable in the tableting process is the compressional pressure, which densifies the powder mass into a dense compact in the die and thus induces bonding inside the compact and formation of strong tablets. There is often a clear correlation between compressional pressure and mechanical strength of the tablets. The proper mechanical strength is an essential property affecting the easiness of packing, transportation, storing as well as administration of tablets. Furthermore, the mechanical strength is correlated with the disintegration of pharmaceutical tablets in gastrointestinal tract and also with release rate of active substance from the dosage form.

Only few commercial excipients are well adapted for slugging or direct compression. The release of the active substance from the tablet is the most critical phenomenon in which the excipients can have remarkable modifiable effects. Suitable excipients may induce controlled release, most often sustained release of active substance from the tablet. Thus, it is possible to affect the absorption properties, rate and site, as well as the level of achieved drug concentration in blood during drug treatment. This is of uttermost importance both in prophylactic and symptonous medication.

Several possible mechanisms are used to achieve controlled release properties in solid dosage forms. Most often compressed tablets are coated in a separate coating process with polymer films. Although this method is appropriate for achieving suitable drug release properties, several disadvantages are involved in the coating processes. The multistage process, including separate tabletting and coating phases with numerous and complicated process variables is highly energy consuming. Although, water is the solvent of choice, even nowadays organic solvents are often used in coating processes. The evaporation of solvents and their possible harmful effects on tablet structure may also restrict the usability of this technique. The controlling and repeatability of the whole manufacturing chain is especially complicated. Often difficulties may arise due to breaking or inhomogenity of a thin coating film. Thus the drug content can be released much more fastly than desired.

It is also known to prepare controlled release preparations by compressing formulations containing matrix forming excipients. Matrix forming substances commercially available include e.g. methacrylate resins, polyvinyl alcohol, polyethylene glycols. Under compression these substances undergo softening, plastic deformation or even melting. Typically the matrix formers are poorly flowing, sticky and smeary substances. Granulation is often an inevitable preprocess prior to compression of formulations containing these substances. Direct compression of these substances in manufacturing scale is hardly possible. Direct processable matrix formers would be important in respect to time and energy saving as well as to better controlling of the whole manufacturing chain. The manufacture of controlled release formulations using a direct compression process is in principle a simple and easily controllable process. Several disadvantageous process factors, e.g. granulation, drying of granules, usage of organic solvents, drying of solvents, can be avoided.

In tableting processes an intact matrix tablet is formed, in which active substance/substances are dispersed. The matrix former should melt, i.e. undergo softening or plastic deformation under pressure. The structure of the matrix affects the release of the active substance from the matrix tablet. Wettability of tablet surface, penetration of gastric fluids into the tablet matrix, dissolution of the active substance inside the matrix as well as diffusion of the dissolved substance out from the matrix are all dependent on the chemical, physicochemical and mechanical structure of the matrix tablet. In addition to the properties of matrix former/formers, the process variables during the manufacturing process also affect the structure of the matrix tablet as well as the biopharmaceutical properties of the preparation.

The controlled release of the active substances from the preparation is especially important in the administration of the therapeutical substances, i.e. the drugs. If the biological half life of the drug is short, the administration in a controlled release dosage form can lengthen the dosing intervals, thus, enhancing the patient compliance toward drug therapy. Furthermore, the sustained absorption of the drug from the controlled release dosage form maintains the drug concentration in blood in a more steady level and thus the harmful fluctuations in concentrations as well as drug response can be avoided. The use of controlled release dosage forms decreases also the drug amount in contact with the biological membranes at a certain moment of time. This is important e.g. for administration of drugs with an irritating effect.

A constant rate of drug release from a controlled release dosage form is usually desired. On the other hand, in some cases a relatively large loading dose just after administration followed by slower, typically constant drug release as a maintaining dose is desired. In some special cases the slow initial release followed by accelerated release is the profile of choice. This is advantageous, if the drug substance is unstable in the stomach, but more resistant in the intestine. Some drugs are also more effectively absorbed e.g. in colon. The modified release profiles might be beneficial also in diseases with symptoms appearing only at day or night time.

As a conclusion, the desired release profile of the administered drug is dependent on the drug substance and the disease. It is beneficial, if the widely modifiable release properties can be produced using a simple manufacturing procedure and simple construction of preparation consisting of few excipients. Although, the above mentioned text mainly deals with pharmaceutical dosage forms, especially tablets, the same properties are important also for fertilizer, herbicidal and diagnostic preparations.

THE SUMMARY OF THE INVENTION

The present invention provides for use especially in the manufacturing of pharmaceutical preparations and for the controlled release of active ingredients an excipient, i.e. a starch acetate with a distinct degree of substitution. Based on the use of said starch acetate, pharmaceutical or drug preparations with different properties can be manufactured. It is a characteristic of the present invention that the manufacturing can be performed in one stage or a limited number of process stages or steps. The preferred excipient has extraordinary advantageous flowability and bond forming properties and it can act both as a filler and as a binder in the compact, whereby making the compression process more feasible. The substance is convenient for direct compression but it can also be used as an excipient in granulation, dry granulation, slugging or compaction granulation. By controlling the compression force during the manufacturing process it is possible to influence the rate of release of the active ingredient from the preparation and thus to obtain a desired and versatile, modifiable rate of release of the drug in body fluids and absorption into the blood circulation. Thus, according to the present invention it is possible to obtain with one single excipient or with a mixture of different excipients an optimal processing and a preparation with widely modifiable properties.

For those skilled in the art it is evident that the principles described above, which are suitable for drugs can be applied also in other fields, in which the controlled release of an active ingredient should be controlled or the preparation containing the active ingredient should have distinct, closely defined properties.

The excipient according to the invention has advantageous particle properties (size, size range, shape etc.). This gives the preparation the unique properties (flowability, compatibility, compactibility, homogenity of matrix structure etc.).

When the method of the present invention is used physically acceptable starch acetate powders are obtained, the properties of which are more closely defined in the claims. By optimizing the substitution degree of the starch acetate, or the proportional amounts of differently substituted starch acetates in a powder mixture or adjusting the amount of the drug or active ingredient in the formulation the dimensions of the compact or the compressional force the release profile, which is typical for the preparation according to the present invention is achieved. Sustained release rate profiles, constant rate profiles or gradually sustaining and at a certain stage accelerating drug release profiles are possible to obtain.

When the excipient of the present invention are used, preparations or tablets with sustained or prolonged release properties can be easily manufactured by direct compressing techniques. The technical properties of the preparations are advantageous and the starch acetate acts in the preparation in several different ways, e.g. as an excipient with good flowability, but also as a filler, binder, matrix-forming agent and/or modifier of controlled release properties.

Another object achieved by the present invention is that the whole process can be performed in principle in one or in a limited number of steps. Direct compression makes it possible to proceed without wet granulation or dry granulation. By using the composition and method of the invention a small group of excipients are sufficient and problems related to incompatibility decrease. However, the composition according to the present invention does not exclude the possibility of using it in conventional granulation and tabletting processes.

The composition of the present invention is suitable for dry granulation as well as for direct compression. By the aid of the method according to the present invention the desired matrix structure is obtained.

The method of the present invention produces starch acetate powders with the physically optimal properties, i.e. advantageous flowability, compatibility and compactability as well as other important features.

The present invention is thus related to a new type of composition with modifiable properties, which comprises an active ingredient and starch acetate as a compact for industrial use especially intended for controlled release. More specifically the present invention is related to solid dosage forms, especially compacts or tablets for pharmaceutical substances, in which the industrial processability is enabled by starch acetate with a distinct substitution degree, with good flowability and bond forming properties when tabletted as well as properties, which regulate the controlled release of the active ingredient. The invention is also related to the preparation and use of the composition.

THE DETAILED DESCRIPTION OF THE INVENTION

Figure 1:
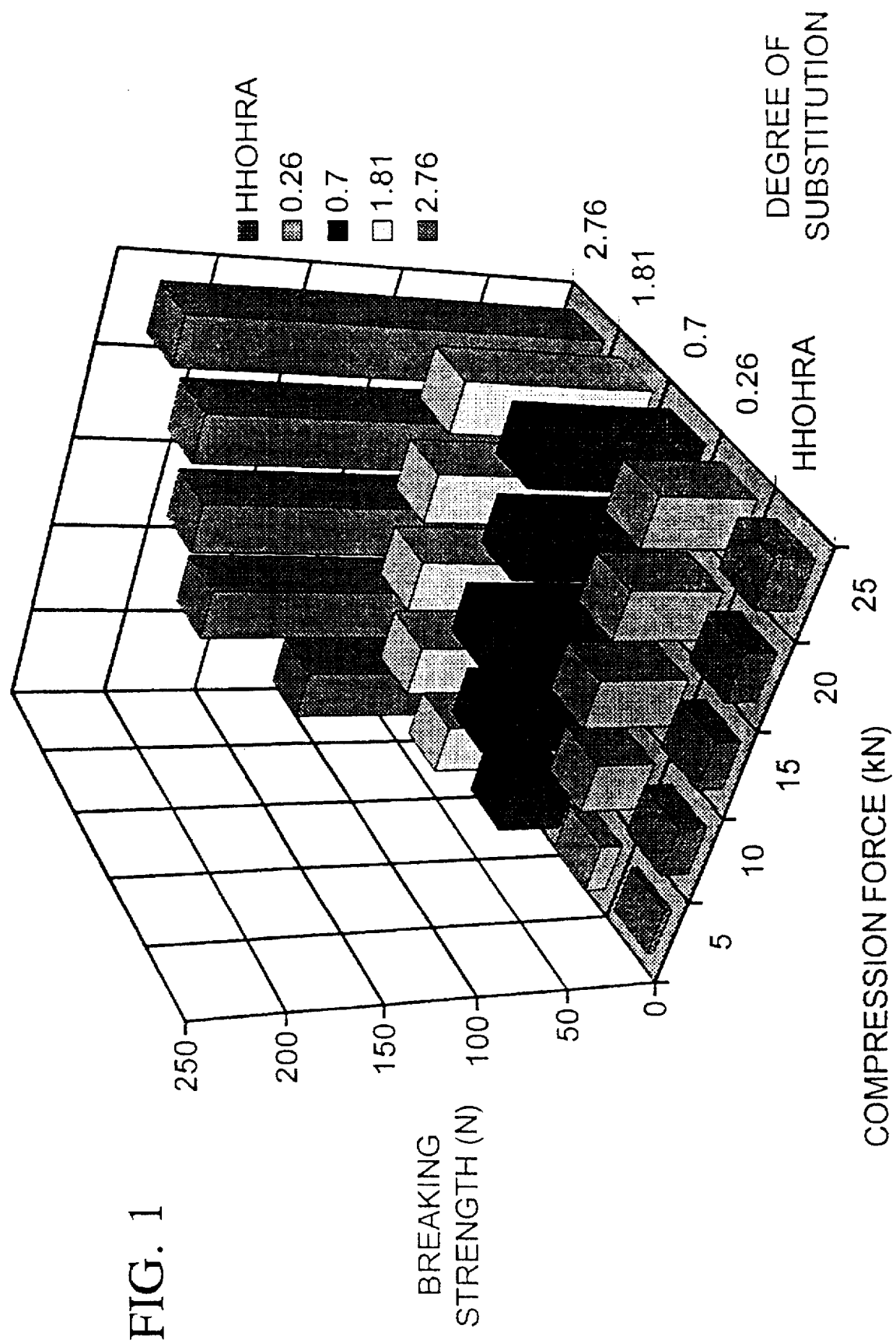
FIG. 1 depicts mechanical strength measured as breaking strength values of tablets made of starch acetate with different degrees of substitution and acid hydrolysed barley starch (HHOHRA) using five compressional forces.

In the following some definitions are given and the composition of the present invention is described in more detail.

A compact means a compressed or compacted tablet-like composition or formulation manufactured from a powder, granules, pellets, microspheres or microcapsules. In this patent application it comprises one or more starch acetates with defined properties and one or more active ingredients.

Active ingredient means a substance or mixture of substances which have a desired effect.

The treatment of barley starch or acid hydrolysed barley starch with acetic anhydrides in the presence of catalysts gives starch acetates with different substitution degrees of which gives the product of the present invention the following properties:

The mechanical strength of the compacted tablets measured as breaking strength and friability increases essentially when the substitution degree increases.

The structure of the tablet changes gradually from compacts of separated deformed particles to a homogenous polymer matrix form when the substitution degree increases.

The disintegration of tablets made of starch acetates with low substitution degrees is extremely rapid, but tablets made from starch acetate with a high substitution degree desintegrates extremely slow in water or digestive fluids.

The drug release changes gradually from the rapid release in tablets with low substitution degrees to slow release from tablets with high substitution degrees.

The properties mentioned above facilitates the use of starch acetate according to its substitution degree so that substitution degrees under about 0.2, preferably under about 0.7 are suitable mainly as disintegrants and fillers in tablets, while derivatives with substitution degrees of about 0.2–3.0, preferably of about 0.7–3.0 are suitable mainly as binders for the tablets, while derivatives with substitution degrees of about 0.7–3.0, preferably about 1.50–3.0, most preferably about 1.8–3.0 are most suitable for controlled release of drugs, fertilizers, herbicides and/or diagnostic substances. It is characteristic for the present invention that all these excipient functions are diffuse and modifiable by changing the parameters in the claims. For example when the substitution degree increases in addition to the binder function the controlled release properties get more prominent.

The preparation according to the invention is a modifiable composition as regards its properties. The main characteristic of the invention is that generally only two components are needed to achieve the variable properties of the composition. By this we mean that the main component of the composition, starch acetate acts as a disintegrate, filler, binder and regulator of the controlled release. When the substitution degree is below about 0.2, preferably below about 0.7 starch acetate functions mainly as a disintegrant or filler. When the substitution degree is about 0.2–3.0, preferably about 0.7–3.0, most preferably below about 1.8 starch acetate functions mainly as a binder and when the substitution degree is about 0.7–3.0, most preferably about 1.8–2.8 starch acetate functions mainly as a regulator of the controlled release of the active ingredient. One of the most characteristic features of the invention is that the excipient functions are diffuse.

The composition of the present invention is typically a compact or tablet, which in addition to one or more active ingredients comprises starch acetate, which composition can be modified to be suitable for different uses by changing the substitution degree, molar mass or by changing the compressional force used in the method of manufacturing.

The substitution degree of the starch acetate varies between about 0.2–3.0. The number average molar mass (Mn) varies between 10 000–250 000, preferably between 50 000–220 000 g/mol and weight average molar mass (Mw) 500 000–40 000 000 g/mol.

The composition of the present invention can be modified by changing the amount of the active/ingredient. A suitable range for the variation for the amount of starch acetate is about 10–99% (w/w) and correspondingly 1–10% for active ingredient. These ranges are approximate references and naturally they vary for different active ingredients. If the drug is very active, amounts of about 0.001% (w/w), preferably 0.01% (w/w) are sufficient.

It is characteristic for the composition of the present invention that it is a compact suitable for the controlled release of an active ingredient, in which compact the substitution degree of starch acetate is about 0.2–3.0, preferably about 0.7–3.0.

The controlled release of the active ingredient can be more closely controlled by using at least two different types of starch acetate with different substitution degrees.

The objective of the present invention can be achieved with compositions with breaking strengths sufficient for practical purposes.

The controlled release of the active ingredient can be affected by varying the amount of the active ingredient. The higher the amount of active ingredient present is, the faster it is released. A certain minimum amount of starch acetate is in any case required, e.g. 50% (w/w). It is preferred that the amount of starch acetate varies between about 70–99% (w/w).

It is characteristic for the composition of the present invention that its properties are modifiable in a desired and controllable way by changing a few parameters. For example, by changing the substitution degree of starch acetate and by changing the compression force compacts are obtained, from which the release of the respective active ingredient is suitable for its respective usage.

In principle, all starches, also native barley, oats, wheat, potato and corn starch are suitable for the preparation of composition according to the present invention, but acid hydrolysed starches are especially suitable for the preparation of the composition according to the present invention. It is, however, especially preferable to produce the starch acetate used in the present invention from acid hydrolysed starch, especially from starch of barley or oats. Starches from barley and oats have a relatively low amylose content, which is about 20–30% (w/w), more exactly 22–28 (w/w), most specifically about 25–27% (w/w).

It is characteristic for the method of the invention that it is, in principle, a one stage direct compressing method, in which at least one active ingredient and starch acetate the substitution degree of which is between about 0.2–3.0, preferably 0.7–2.6 is used.

Though, the principally one stage, direct compressing or tabletting technique is characteristic of the invention, it is not out of the question that the invention can be performed also in conventional compressing and granulation techniques.

When the substitution degree is about 0.7–3.0 and compresing is performed with suitable forces, e.g. 5–30 kN, preferably 10–25 kN, a compact suitable for the controlled release of an active ingredient is obtained.

Also starch acetates with different substitution degrees can be mixed together in which case the controlled release can be even more exactly controlled. The release can be further regulated by varying the amount of the active ingredient.

The compositions of the present invention are especially suitable for pharmaceutical products, such as tablets, but they can also be used to prepare granulates, pellets or tablets containing fertilizers, herbicides, diagnostic substances.

In the composition of the present invention it is possible to use different active substances. Suitable therapeutically active ingredients, which are useful in the present invention are for example β-adrenoceptor blocking agents, analgetics, anti-arrhytmic agents, antibacterial agents, anticonvulsives, antidepressants, antihistamines, antihypertensives, antipsychotics, antiulcer drugs, bronchodilators, diuretics, hypoglycaemics, parasympathomimetics, vasodilators, etc.

In the composition of the present invention primary fertilizers, such as nitrogen, phosphor and potassium etc., or secondary fertilizers such as calcium, magnesium and sulphour etc. or micronutrients such as iron, mangan, copper etc. can be used.

The composition can also be used for controlled release of herbicides, fungicides and other toxic substances. It is also applicable as a carrier for reagents in diagnostic devices.

In the following the invention is described in more detail by the aid of examples without limiting the scope of the protection:

EXAMPLE 1

Preparation of starch acetate

Starch acetate was prepared according to the method described in the patent U.S. Pat. No. 3,795,670 by changing the amount of base used as a catalyst and reaction time. The method of the patent mentioned was somewhat changed by using smaller amounts of catalyst and lower temperatures for the addition of the catalyst. In the examples barley starch has been used as a model starch. The effect of the molar mass of starch on the reaction is studied by the aid of acid hydrolysed barley starch.

In the examples highly hydrolysed barley starch has been used, but starches, which are not so highly hydrolysed act in the same way. For this reason the hydrolyses of starch and method of preparation for starch acetate, which are described below are examples only. For a person skilled in the art, it is evident that different known and novel hydrolysis and acetylating methods can be used to achieve the same result. In these examples the same reaction model was adapted for all starches.

Hydrolyses of starch

Hydrolysed starch was prepared from native starch by suspending 1 000 g starch in 1 200 ml 1.4M hydrochloric acid and heating the suspension by mixing 3 hours at 45° C. After the hydrolysis the product was neutralized with dilute sodium-hydroxide, filtrated and thoroughly washed with water and dried.

In the esterification the amounts of reagents used are shown in Table 1.

The starch and acetic acid anhydride was added into a flask provided with a mechanical stirrer, reflux condenser, drop funnel and thermometer. The stirrer was turned on and the temperature of the mixture was raised to 60° C. Into the mixture 50% (w/w) sodium hydroxide-water solution was added drop by drop. The temperature of the reaction mixture raised about 40–60 degrees during the addition. After all NaOH was added, the temperature of the reaction mixture was raised to 125° C.: een and held at that temperature the time indicated in Table 1.

After the reaction had taken place the mixture was cooled and the starch acetate was precipitated from water with vigorous mixing. The precipitate was filtered and washed thoroughly with water until pH was >5.

TABLE 1

| Starch acetate Batch No. | Starch | Acetanhydride g | NaOH 50% | Reaction times h |
|---|---|---|---|---|
| 1 | Hydrolysed barley starch 500 | 2000 | 110.0 g | 5 |
| 2 | Hydrolysed barley starch 500 | 2000 | 90.0 g | 5 |
| 3 | Hydrolysed barley starch 500 | 2000 | 35 ml | 5 |
| 4 | Hydrolysed barley starch 500 | 2000 | 35 ml | 1 |
| 5 | Native barley starch 450 | 2000 | 99.0 g | 5 |
| 6 | Native barley starch 500 | 2000 | 84.1 ml | 5 |
| 7 | Native barley starch 500 | 2000 | 35 ml | 1 |
| 8 | Native barley starch 50 | 200 | 5.2 g | 5 |

The properties of the products are shown in Table 2:

TABLE 2

| Starch acet. No. | Subst. degree DS | Dry matter % | Ash % | Molar mass g/mole | |
|---|---|---|---|---|---|
| 1 | 2.76 | 98.5 | 0.10 | Mn | 53 000 |
|   |      |      |      | Mw | 1 100 000 |
| 2 | 1.81 | 98.2 | 0.14 | Mn | 53 000 |
|   |      |      |      | Mw | 1 100 000 |
| 3 | 1.71 | 91.8 | 0.13 | Mn | 53 000 |
|   |      |      |      | Mw | 1 100 000 |
| 4 | 0.26 | 90.4 | 0.14 | Mn | 53 000 |
|   |      |      |      | Mw | 1 100 000 |
| 5 | 2.68 | 97.8 | 0.10 | Mn | 220 700 |
|   |      |      |      | Mw | 36 060 000 |
| 6 | 0.97 | 94.4 | 0.15 | Mn | 220 700 |
|   |      |      |      | Mw | 36 060 000 |
| 7 | 0.32 | 91.4 | 0.20 | Mn | 220 700 |
|   |      |      |      | Mw | 36 060 000 |
| 8 | 1.76 | 98.1 | 0.17 | Mn | 220 700 |
|   |      |      |      | Mw | 36 060 000 |

The determination of the substitution degree was done as described in the publication Wurzburg, O. B. "Acetylation", in the book "Methods in Carbohydrate Chemistry" Vol. IV, Ed. R. L. Whistler, Academic Press, New York & London, 1964, p. 288.

The molar mass was determined by the aid of GPC-analyses in the Research Laboratory of Oy Alko Ab, using the apparatus HP-1090, with two columns of the Series (Waters, Ultra Hydrogel 2000) solvent 50 mM NaOH, temperature 40° C., dextran standards, detectors RI- and viscosity-detectors. The molar masses are determined from the starch used as starting material.

EXAMPLE 2

Compression of tablets

A series of starch acetate, with different degree of substitution, tablets were compressed with an instrumented eccentric tablet press (Korsch, EK-0, Berlin, Germany) using flat-faced punches with a diameter of 1 cm. The rate of the tablet press was 30 rpm. The compression forces used in this study were 5, 10, 15, 20 and 25 kN. Before compression all powders were stored for not less than three days at 33% relative humidity and room temperature. Pre-weighed powder samples were poured manually into the die cavity. For each material, tablet weights were adjusted to produce compacts with the same thickness of 0.125 cm by using densities of each different materials. Tablets were compressed without lubrication.

EXAMPLE 3

Mechanical properties of tablets

After compression tablets were stored at 33% relative humidity for not less than 24 hours before measuring the weight, dimensions and radial breaking strength of tablets. Ten tablets of each material were weighed using the analytical balance and their diameter and thickness were measured with a micrometer. The radial breaking strength of six tablets were determined using a CT-5-tester (Engineering Systems, Nottingham, England). The breaking strengths of starch acetate tablets with different degree of substitution are shown in Table 3.

The friability of tablets were examined with a Roche-friabilator. Six pre-weighed tablets of each starch acetate were placed in the friabilator, which was then operated for four minutes (100 revolutions). Afterwards tablets were dusted and reweighed with an analytical balance. The loss of weight for each batch was calculated in percent (Table 3.).

Figure 2:
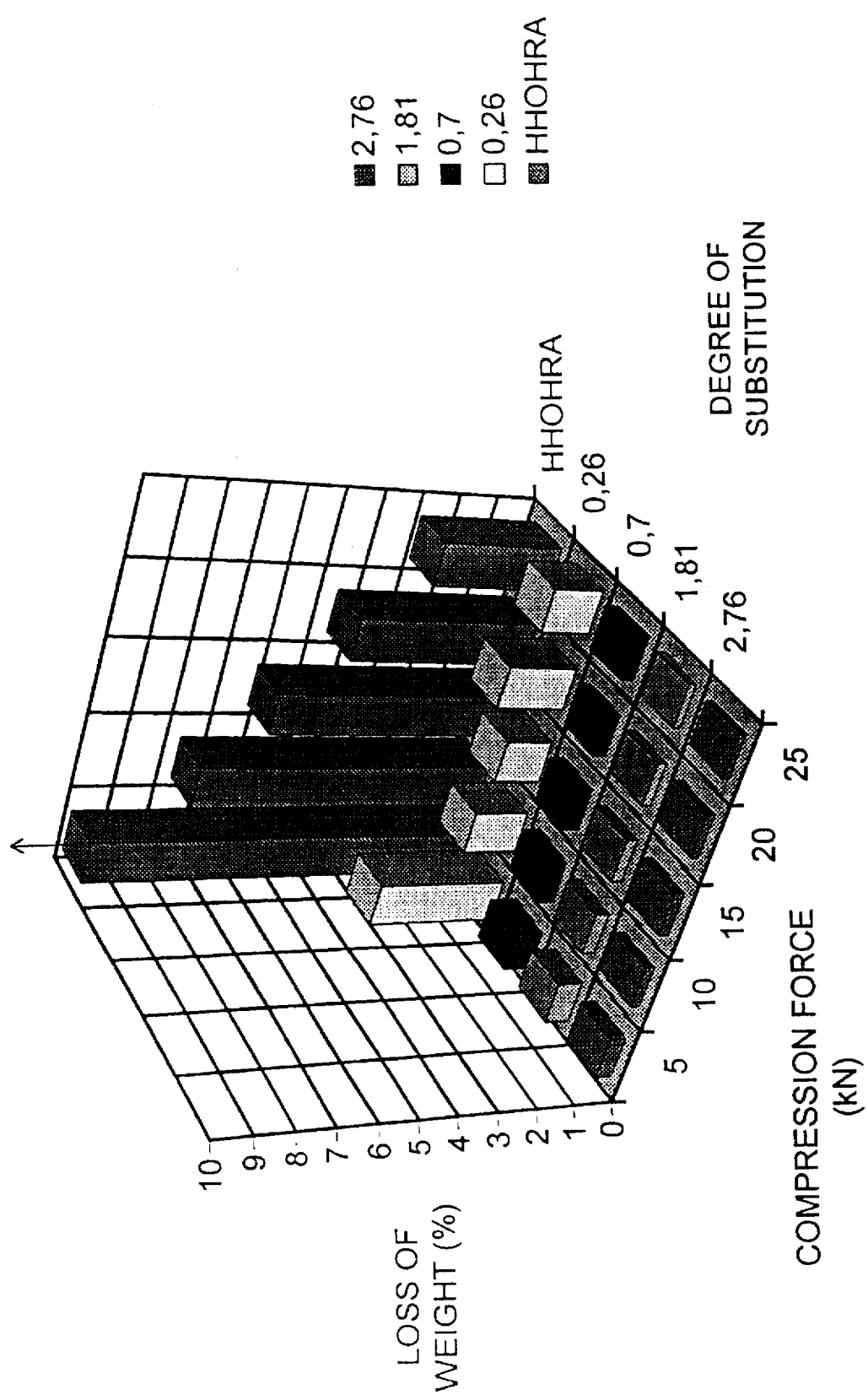
FIG. 2 depicts abrasion resistance in a friability test measured as weight loss, release and abrasion resistance of tablets prepared from starch acetate tablets with different substitution degrees and acid hydrolysed barley starch (HHOHRA).

The breaking strength of starch acetate tablets increases as the degree of substitution increases (FIG. 1, Table 3). Both low and high substituted starch acetates seem to have an ability to form tough tablets even at relatively low compression force. The weight loss of starch acetate tablets decreases with increasing degree of substitution (FIG. 2, Table 3). Both breaking strength and friability of starch acetate tablets increase as compression force rises.

EXAMPLE 4

The microstructure of tablets

Figure 3A:
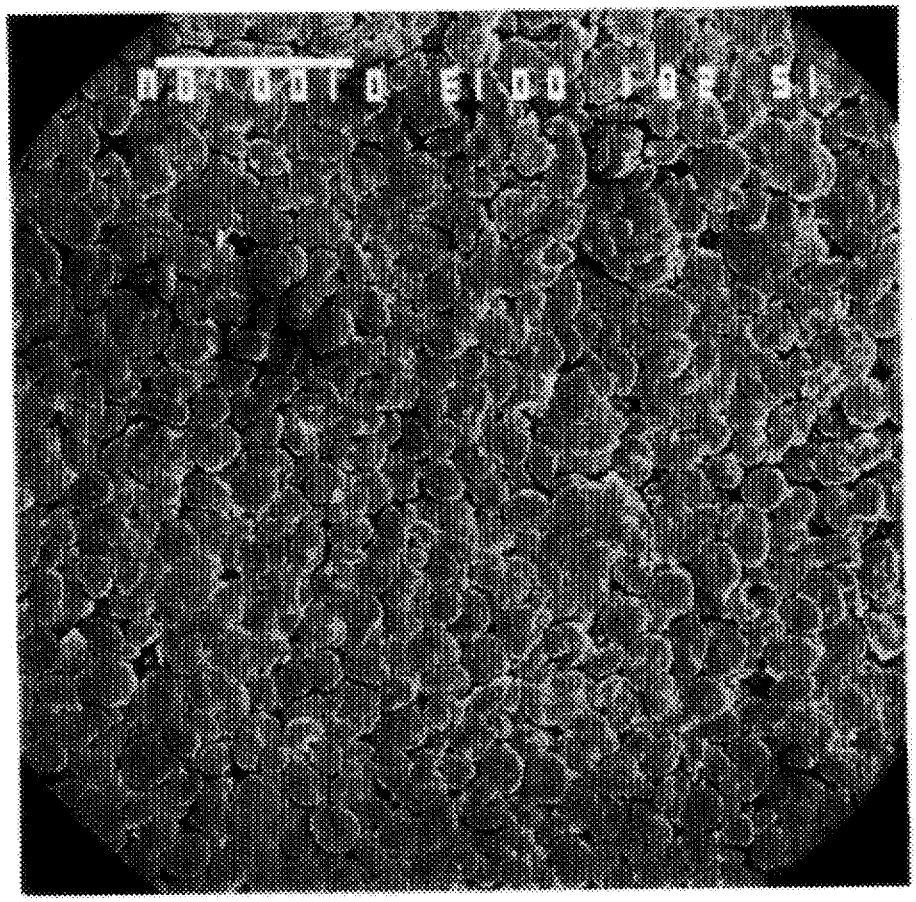
FIG. 3A depicts the surface of a tablet of starch acetate when the substitution degree is 0.26. The bar is 100 µm.
Figure 3B:
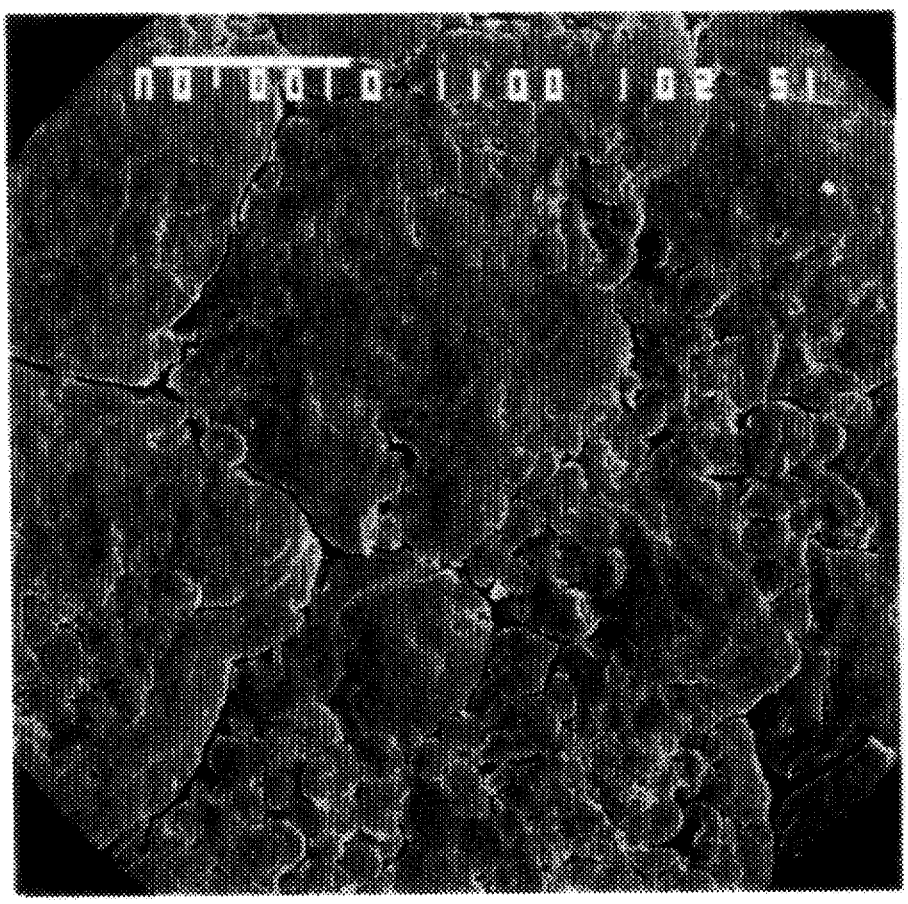
FIG. 3B depicts the surface of a tablet of starch acetate when the substitution degree is 0.7. The bar is 100 µm.
Figure 3C:
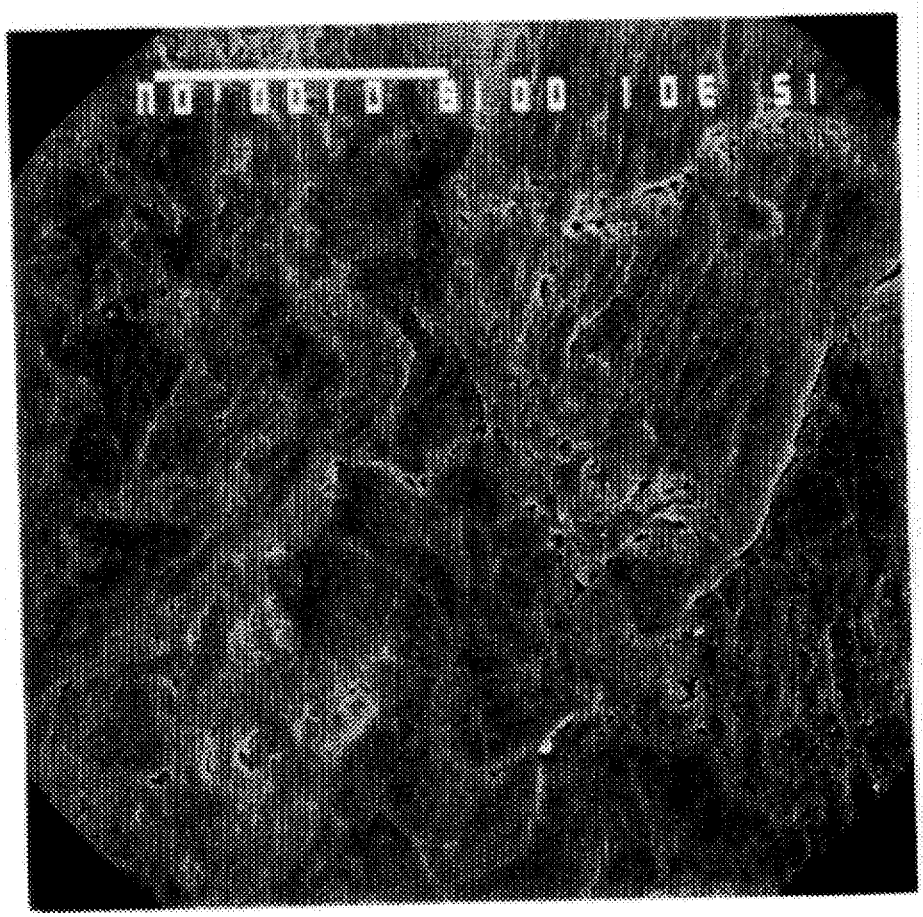
FIG. 3C depicts the surface of a tablet of starch acetate when the substitution degree is 2.76. The bar is 100 µm.

Starch acetate tablets with different degree of substitution were sputter coated with gold and upper surfaces of tablets were photographed using an electron scanning microscope (Jeol JSM 35, Tokyo, Japan). The microstructure of the upper surface of starch acetate tablets changes gradually as the degree of substitution increases (FIG. 3). The starch acetate with the degree of substitution 2.76, seem to form homogenous polymer matrix type of structure (FIG. 3c). As the starch acetate is lower separate deformed particles in the surface of tablets can be seen (FIGS. 3a and 3b).

EXAMPLE 5

Disintegration time of tablets

The disintegration time of tablets was determined using the method described in the European Pharmacopoeia (Ph. Eur., V.5.1.1.). Instead of water, both simulated gastric fluid (without pepsin) and intestine fluid (without pancreatin) were used as disintegration medium. pH values were 1.2 and 7.5 for gastric fluid and intestine fluid, respectively. The disintegration time for each starch acetate tablet batch was calculated in the mean of three determinations.

Figure 4:
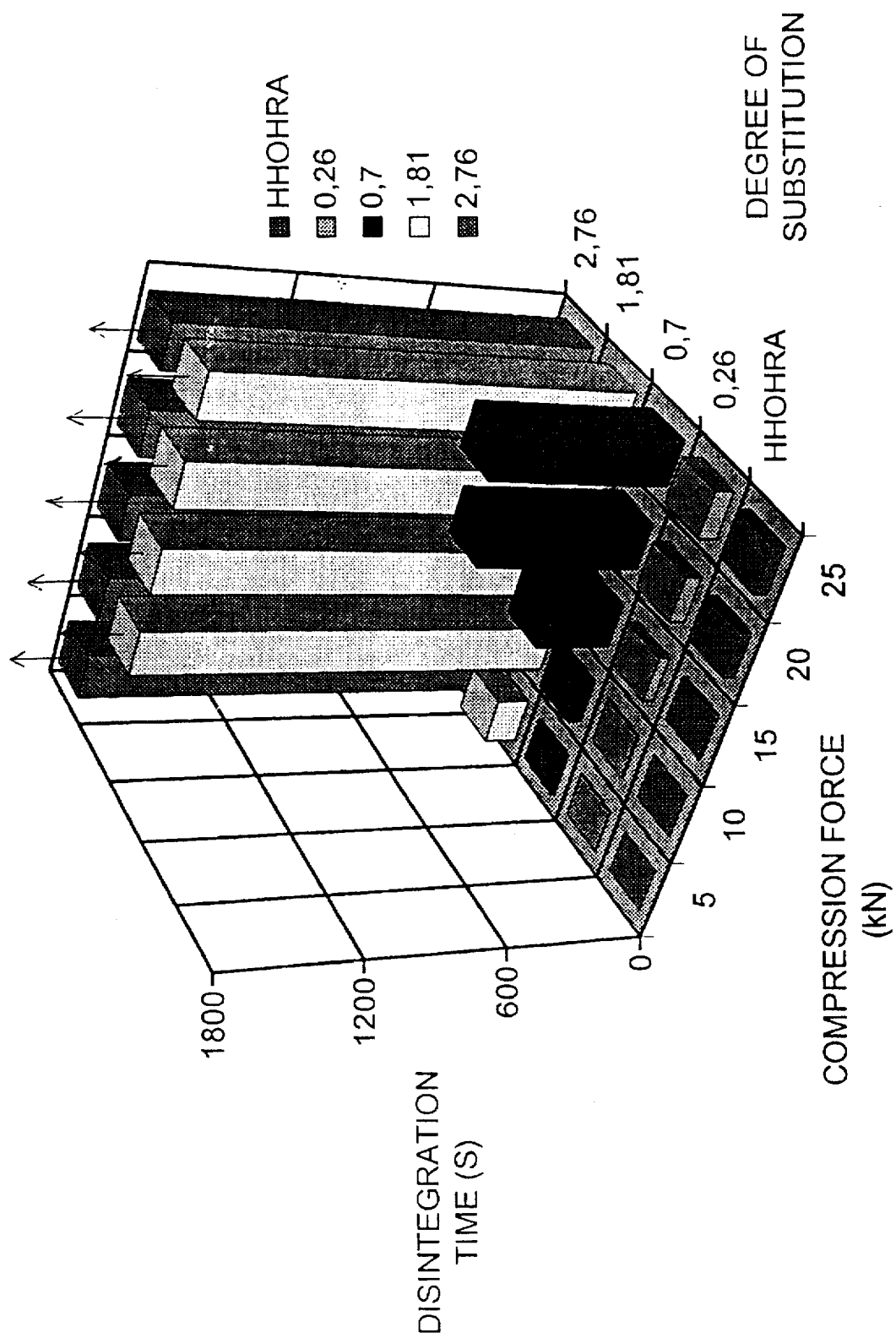
FIG. 4 depicts disintegration times at pH 1.2 for tablets compressed from starch acetates with different substitution degrees and acid hydrolysed barley starch (HHOHRA) as a control. The tablets were compressed with five different forces.
Figure 5:
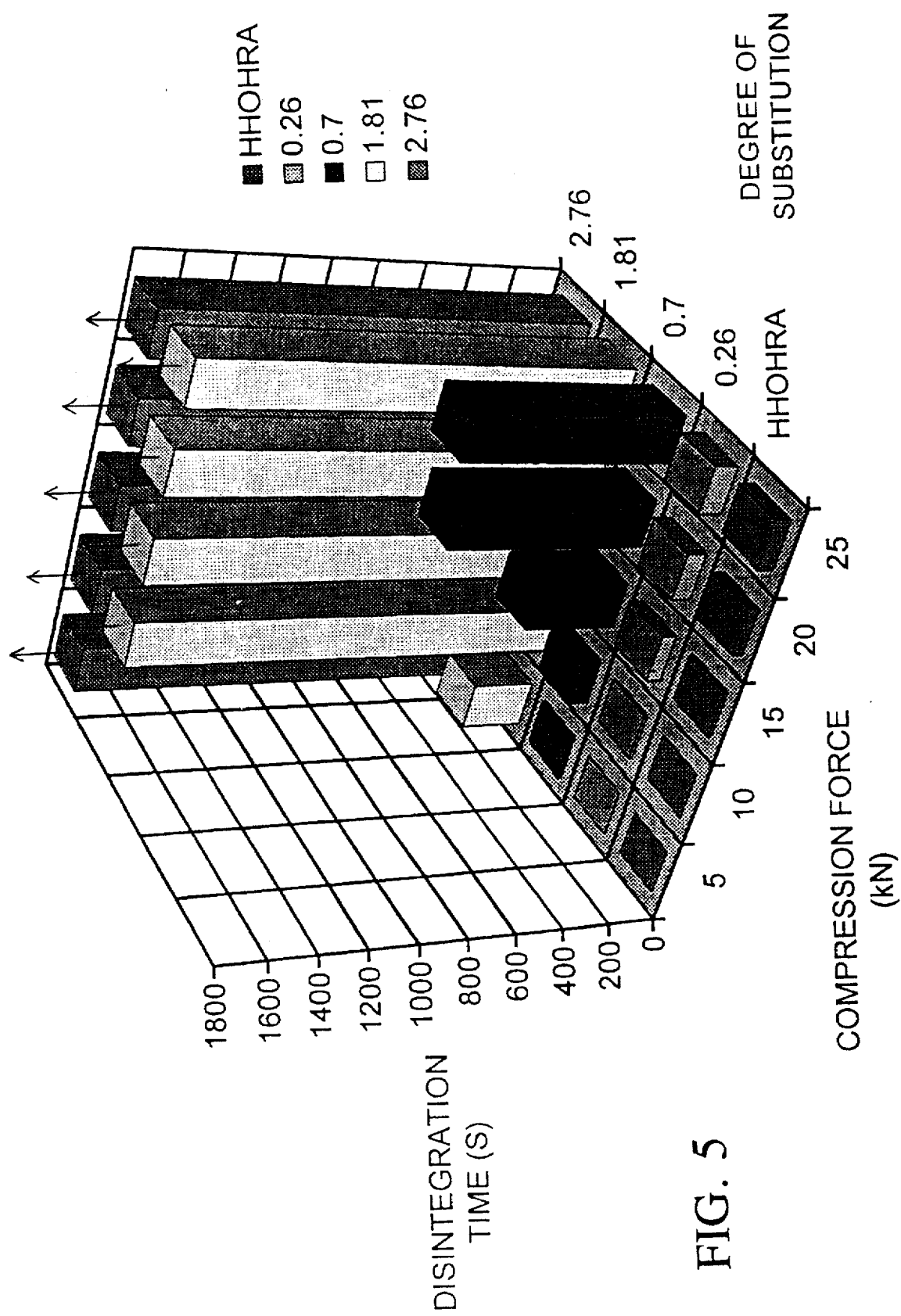
FIG. 5 depicts disintegration times at pH 7.5 for tablets compressed from starch acetates with different substitution degrees and acid hydrolysed barley starch (HHOHRA) as a control. The tablets were compressed with five different forces.

As the compression force rises the disintegration time prolongs regardless of the degree of substitution of starch acetate molecule (FIGS. 4 and 5, Table 3). The prolonging of disintegration time is appreciable as the degree of substitution is above one. The disintegration times of series of starch acetate with different degree of substitution are shown in Table 3.

Regardless of compression force starch acetate tablets with the highest degree of substitution, in this study ie. 2.76, did not disintegrate in thirty minutes. Except those tablets compressed at 5 kN force, starch acetate tablets with the degree of substitution 1.81 did not either disintegrate in thirty minutes. There were no noticeable differences in disintegration times depending on pH value of disintegration medium (FIGS. 4 and 5, Table 3).

TABLE 3

The breaking strength, friability and disintegration time in gastric and intestine fluid of acid hydrolyzed barley starch (HHOHRA) tablets and starch acetate tablets with different degree of substitution. Tablets were compressed at five different compression forces. s is standard deviation.

| Starch acetate | Breaking strength (N) | Friability (%) | Disint. time (min, sec, s) Gastric fluid pH 1.2 | | | Intestine pH 7.5 | | |
|---|---|---|---|---|---|---|---|---|
| | | | min | sec | s | min | sec | s |
| HHOHRA | | | | | | | | |
| 5 kN | 4.0 | 27.8 | — | — | — | — | — | — |
| 10 | 15.2 | 7.8 | | 4 | 0.6 | — | — | — |
| 15 | 14.4 | 6.3 | | 15 | 3 | | 15 | 6.7 |
| 20 | 18.4 | 4.7 | | 52 | 8.3 | | 47 | 1.2 |
| 25 | 22.0 | 3.1 | | 58 | 6.4 | 1 | 12 | 8.2 |
| No. 4 DS 0.26 | | | | | | | | |
| 5 kN | 12.1 | 3.4 | | 5 | 2.3 | | 4 | 1.3 |
| 10 | 32.5 | 1.4 | | 10 | | | 13 | 4.3 |
| 15 | 49.1 | 1.2 | | 47 | 3.1 | 1 | 3 | 12.1 |
| 20 | 51.1 | 1.8 | 1 | 8 | 4.6 | 1 | 22 | 2.1 |
| 25 | 54.8 | 1.3 | 1 | 23 | 11.5 | 1 | 37 | 3.2 |
| No. 3 DS 0.7 | | | | | | | | |
| 5 kN | 36.8 | 0.71 | | 15 | 2.1 | | 17 | 3.2 |
| 10 | 63.7 | 0.47 | 1 | 6 | 15.1 | | 26 | 52.4 |
| 15 | 80.3 | 0.43 | 5 | 37 | 34.5 | 6 | 32 | 202.7 |
| 20 | 79.6 | 0.32 | 11 | 58 | 119.5 | 13 | 54 | 155.9 |
| 25 | 87.9 | 0.33 | 13 | 6 | 56.8 | 14 | 46 | 44.2 |
| NO. 2 DS 1.81 | | | | | | | | |
| 5 kN | 50.1 | 0.65 | 2 | 25 | 18.1 | 4 | 25 | 1.1 |
| 10 | 82.3 | 0.33 | >30 | | | >30 | | |
| 15 | 97.2 | 0.27 | >30 | | | >30 | | |
| 20 | 104 | 0.22 | >30 | | | >30 | | |
| 25 | 105.4 | 0.19 | >30 | | | >30 | | |
| No. 1 DS 2.76 | | | | | | | | |
| 5 kN | 109.6 | 0.40 | >30 | | | >30 | | |
| 10 | 178.3 | 0.22 | >30 | | | >30 | | |
| 15 | 195.9 | 0.25 | >30 | | | >30 | | |
| 20 | 207.5 | 0.20 | >30 | | | >30 | | |
| 25 | 229.8 | 0.17 | >30 | | | >30 | | |

EXAMPLE 6

Dissolution test

Starch acetate with different degree of substitution and propranolol hydrochloride (Batch L0102, AMSA, Milan, Italy) were compressed using an instrumented eccentric tablet press. Drug and lubricant magnesium stearate contents in each tablet were 25% (w/w) and 0.5% (w/w), respectively. The compression force used to form tablets was about 15 kN. The die and punch set as well as the rate of the tablet press were same as described earlier (Example 2).

The dissolution tests were performed using the USP rotating basket method (USP XXII) at the rotation speed of 100 rpm. 300 ml of phosphate buffer of pH value 7 was used as dissolution medium. The ionic strength of dissolution medium was 40 mM. Samples of 3 ml were withdrawn from the vessels at selected intervals, filtered through 0.2 μm membrane filters, suitably diluted with phosphate buffer solution. Propranolol hydrochloride concentration was measured spectrophotometrically at a wavelength of 289 (Hitachi-220, Tokyo, Japan).

Figure 6:
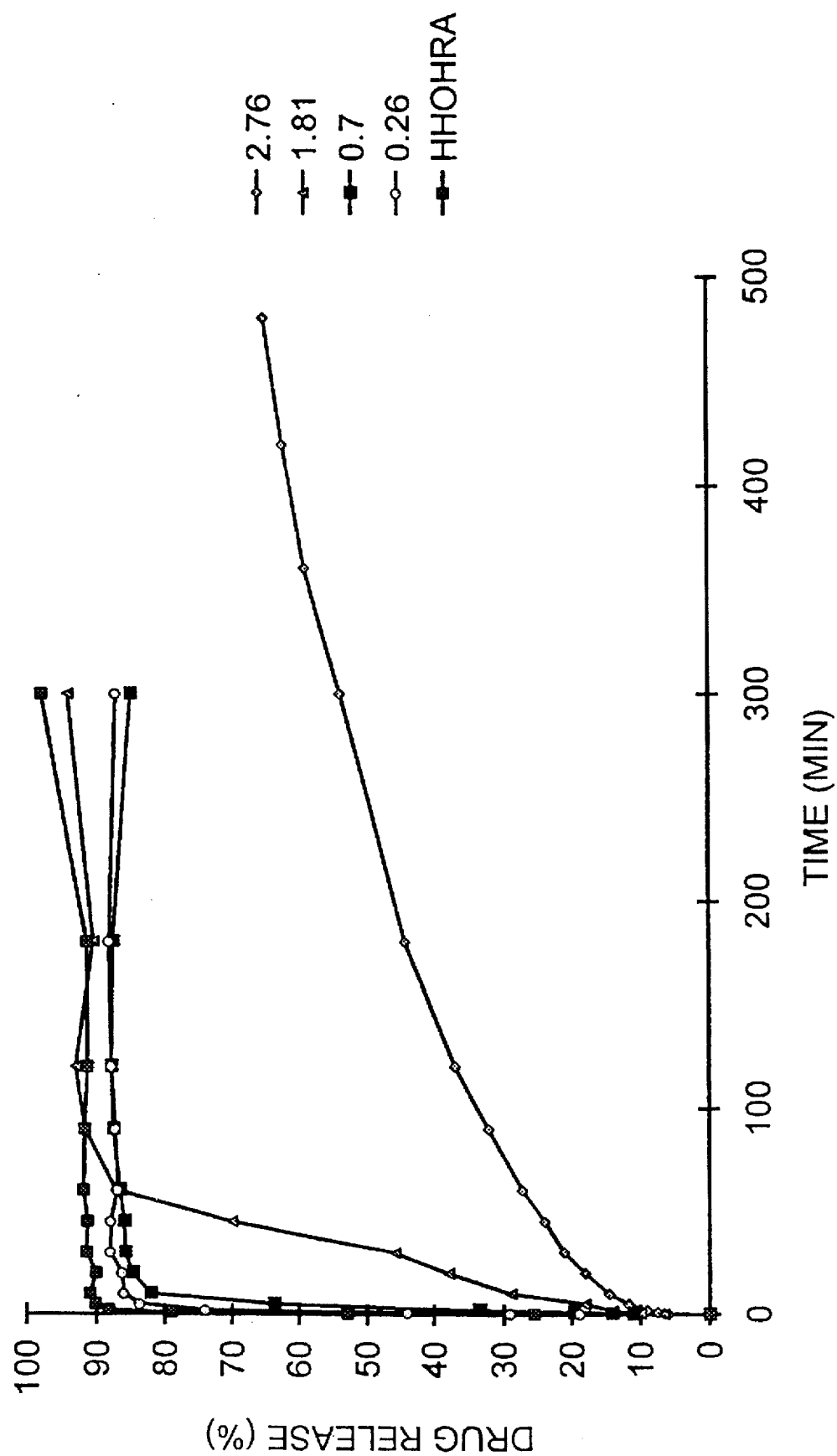
FIG. 6 depicts the drug release in percents as a function of time for tablets compressed from starch acetates with different substitution degrees and acid hydrolysed barley starch (HHOHRA).

Drug release from tablets with low degree of substitution, ie. 0.26 and 0.7, was relatively rapid. In 30 minutes after the experiment was started almost 90% of drug was released from tablets (FIG. 6). As the degree of substitution increases until 1.81, rate of drug release becomes significantly slower. Only about 45% of propranolol hydrochloride of tablets was released in thirty minutes. About 80 minutes were required to release approximately 90 percent of the active ingredient from this type of starch acetate tablet matrix. As the degree of substitution of starch molecule with acetate groups approaches its maximum value, ie. 2.76, the drug release rate decreases dramatically throughout the experiment. During the first thirty minutes of the experiment only 21% percent of propranolol hydrochloride was dissolved from matrix. Dissolution test was ceased after eight hours and at that time the percentage of drug release was about 65%.

EXAMPLE 7

The effect of compression force on the rate of drug release from the starch acetate tablets Starch acetate polymer tablets, containing 25% (w/w) of propranolol hydrochloride as an active ingredient, were compressed at five different compression forces using an instrumented eccentric tablet press. The degree of substitution of polymer was 1.81. 0.5% (w/w) of magnesium stearate was added to perform as a lubricant. The tableting and dissolution test conditions were similar to earlier experiments (Example 2 and 6).

Figure 7:
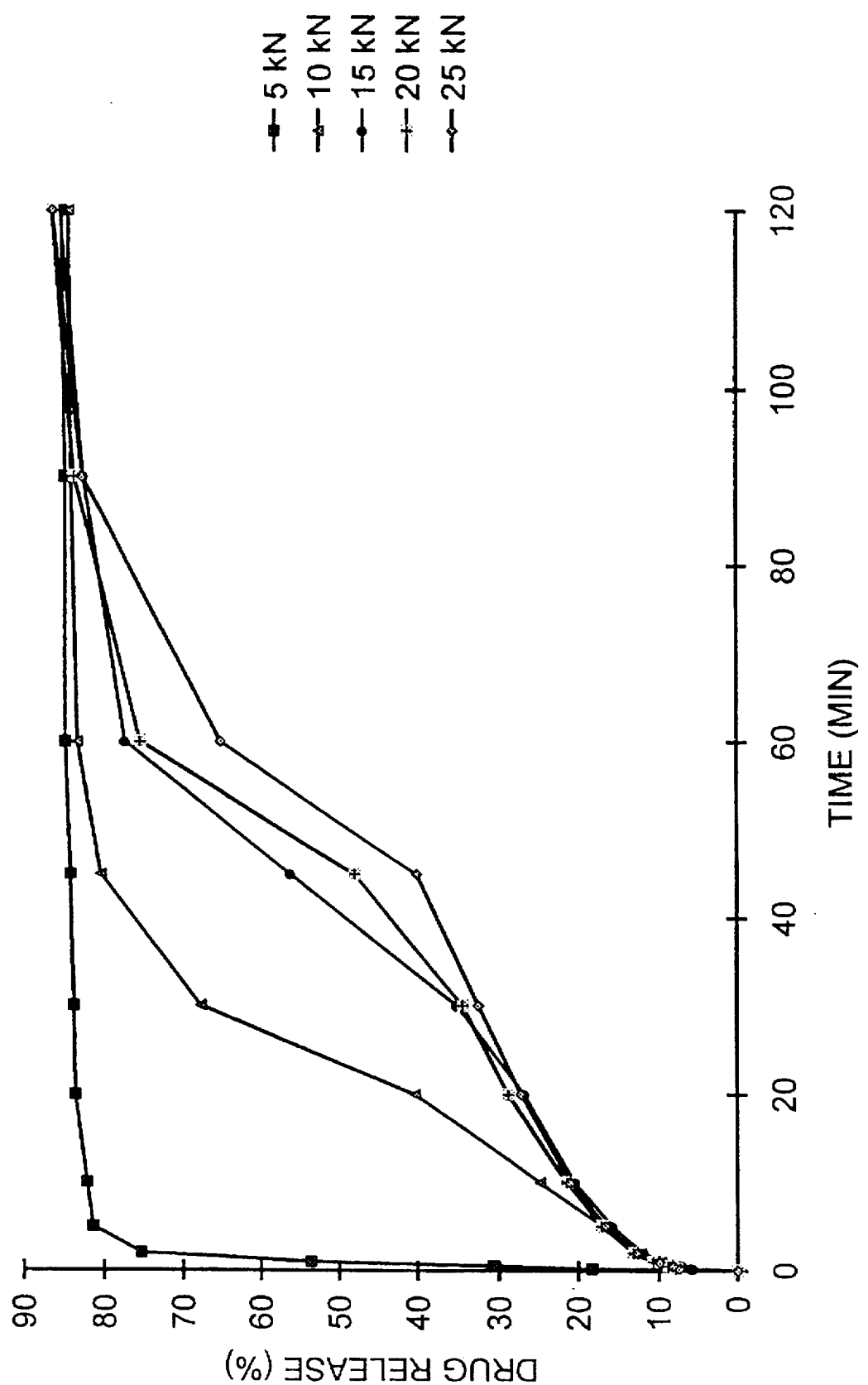
FIG. 7 depicts the drug release in percents as a function of time for tablets compressed from starch acetates with substitution degree of 1.81 using different forces.

The active substance released relatively rapidly from the tablets compressed using the lowest force, ie. 5 kN (FIG. 7). In ten minutes, about 80% of drug ingredient was released from compacts. In the case of tablets, compressed at force of 10 kN, release of propranolol hydrochloride was somewhat slower. Approximately 67% and 80% of drug substance was released in thirty and sixty minutes, respectively. As the compression force was risen to 15 kN and above, ie. 20 and 25 kN, release rate still decreases. Regardless of magnitude of compression force about 30% of model substance was dissolved during the first thirty minutes. As the experiment continued release rate decreases with increasing compression force.

EXAMPLE 8

Drug release from starch propionate and hexanoate matrix

Starch propionate and hexanoate tablets, were compressed at 15 kN force using similar method as described in Example 1. The contents of tablet was 74.5% polymer, 25% propranolol hydrochloride and 0.5% magnesium stearate. The degree of substitution of polymers was three. The breaking strength and disintegration time of tablets were determined.

Figure 8:
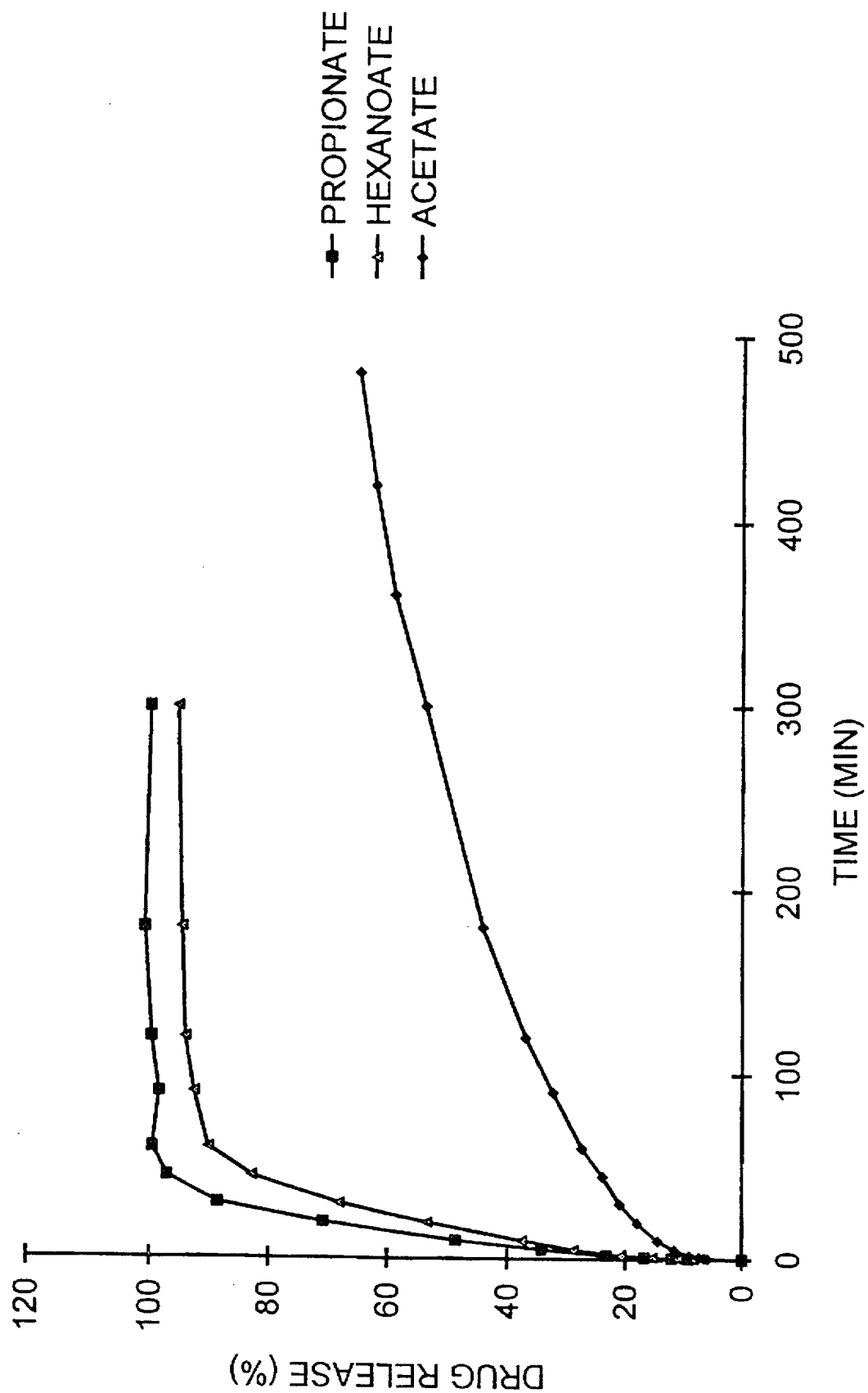
FIG. 8 depicts the drug release in percents as a function of time for tablets of starch acetates (3.0), -hexanoates (3.0) and -propionates (3.0) with substitution degree in parenthesis.

The drug release was examined using identical dissolution test procedure as described previously. The rate of drug release of starch propionate and hexanoate tablets was compared to release properties of starch acetate tablets, with the degree of substitution 2.76 (FIG. 8). The release of active substance was faster from a starch propionate and hexanoate polymer matrix than from starch acetate tablets, with that particular degree of substitution. The percentage of released propranolol hydrochloride after thirty minutes was nearly 90% and 70% for starch propionate tablets and starch hexanoate tablets, respectively. About ninety minutes was required for hexanoate tablets to release 90% of the drug content.

Especially starch hexanoate was problematic material concerning compression process. Polymer had a propensity to stick on the metal surfaces of punches and die. Starch propionate also had the same poor property, but was somewhat easier to handle. Both material formed relatively weak tablets (Table 4).

TABLE 4

Compression force, weight, breaking strength and disintegration time of tablets containing starch esters and propranolol hydrochloride.

| Starch ester | Compression force (kN) | Weight (mg) | Breaking strength | Disintegr. time (min) |
|---|---|---|---|---|
| Acetate | 15.0 | 141 | 151 | >120 |
| No. 8* | n = 7 | n = 7 | n = 4 | n = 3 |
| Hexa- | 15.7 | 110 | 26 | >120 |
| noate* | n = 6 | n = 6 | n = 3 | n = 3 |
| Propio- | 14.9 | 121 | 8 | >120 |
| nate* | n = 7 | n = 7 | n = 4 | n = 3 |
| Acetate | 15.1 | 136 | 129 | >120 |
| No. 2** | n = 7 | n = 7 | n = 4 | n = 3 |
| Acetate | 4.9 | 133 | 81 | >120 |
| No. 1*** | n = 7 | n = 7 | n = 3 | n = 3 |
| Acetate | 15.1 | 138 | 97 | >120 |
| No. 4 + 1* | n = 7 | n = 7 | n = 4 | n = 3 |
| Acetate | 14.8 | 138 | 97 | >120 |
| No. 3 + 1* | n = 7 | n = 7 | n = 4 | n = 3 |
| Acetate | 15.8 | 134 | 110 | >120 |
| No. 2 + 1* | n = 7 | n = 7 | n = 4 | n = 3 |
| Acetate | 15.3 | 136 | 85 | 53 |
| No. 2* | n = 6 | n = 6 | n = 3 | n = 3 |

The amount of active ingredient and compression force used in the preparation of tablets in Table 4

* 25% w/w propranolol hydrochloride Compression force 15 kN

** 5% w/w propranolol hydrochloride Compression force 15 kN

*** 25% w/w propranolol hydrochloride Compression force 5 kN

The degrees of substitution of polymers are same as shown in Table 2.

The degree of substitution of propionate and hexanoate esters was 3.0.

The disintegration time was determined using the method presented in European Pharmacopoeia (V.5.1.1.). Hexanoate tablets did not disintegrate in two hours and the experiment was ceased. In the case of propionate polymer tablets broke down in a few pieces after eight minutes. There were still small pieces left in the glass cylinders of apparatus after two hours when the test finished (Table 4).

Thus, only starch acetate functions as was hoped for concerning sustained drug release.

EXAMPLE 9

The effect of drug concentration on the rate of drug release

Starch acetate (degree of substitution 1.81) tablets, containing 5% (w/w) of propranolol hydrochloride as an active substance, were compressed at 15 kN force using an instrumented eccentric tablet press. The dissolution test was performed using a previous method. The disintegration and breaking strength of tablets were also examined.

Figure 9:
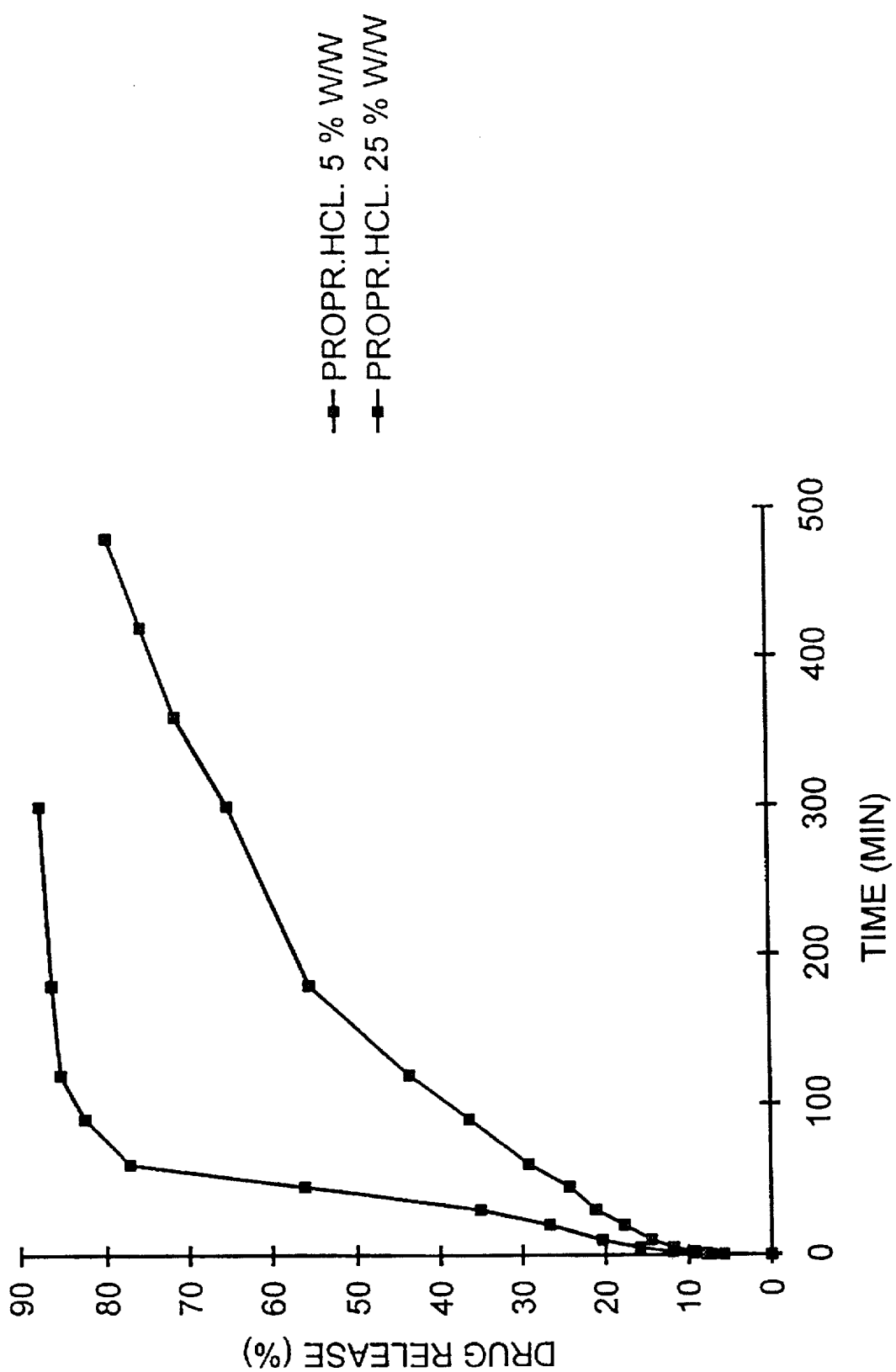
FIG. 9 depicts the release of an active ingredient in percents as a function of time from starch acetate tablets containing either 5 or 25% (w/w) of propranolol hydrochloride.

Drug release from starch acetate tablets containing propranolol hydrochloride either 5% (w/w) or 25% (w/w) is shown in FIG. 9. During the first thirty minutes about 20% of drug content released. The last sample was taken after eight hours and until that time approximately 80% of propranolol hydrochloride was released. The same percentage of drug content was released in sixty minutes as a (in an effective—below minimum effective concentration <--> side-effects, toxic effects—over maximum effective concentration) polymer matrix held drug content of 25% (w/w).

As the drug content increases the breaking strength diminishes. The mean breaking strength of four tablets, containing propranolol hydrochloride 5% (w/w), was 129N. The corresponding value of tablets with 25% (w/w) drug content, was 76N (mean of five determinations). The effect of drug concentration on the disintegration time was examined. The disintegration time reduced as concentration of active substance increased (Table 4 and 5).

TABLE 5

Weight, breaking strength and disintegration time of starch acetate tablets compressed at five different compression force. The degree of substitution of polymer is 1.81. The drug content of tablet is 25% (w/w) of propranolol hydrochloride.

| Compress. force (kN) | Weight (mg) n = 5 | Breaking force (N) n = 5 | Disintegration time (min) n = 3 |
|---|---|---|---|
| 5 | 138 | 25 | 1 |
| 10 | 137 | 64 | 25 |
| 15 | 137 | 76 | 38 |
| 20 | 137 | 85 | 43 |
| 25 | 137 | 83 | 46 |

Thus, it is possible to influence on the rate of drug release of starch acetate tablets with varying relative amount of active substance.

EXAMPLE 10

Drug release from matrix containing equal amounts of starch acetate with different degree of substitution Following physical mixtures containing starch acetate powders with different degree of substitution were prepared:

a) 50% ds. 0.26+50% ds. 2.76 b) 50% ds. 0.70+50% ds. 2.76 c) 50% ds. 1.81+50% ds. 2.76

*ds. degree of substitution

Tablets, compressed with an instrumented eccentric tablet press at 15 kN, contained 74.5% of polymeric mixture, 25% of propranolol hydrochloride and 0.5% of magnesium stearate. The dissolution test were performed using the rotating basket method of USP as previously was represented. The breaking strength and disintegration tests were also performed.

Figure 10:
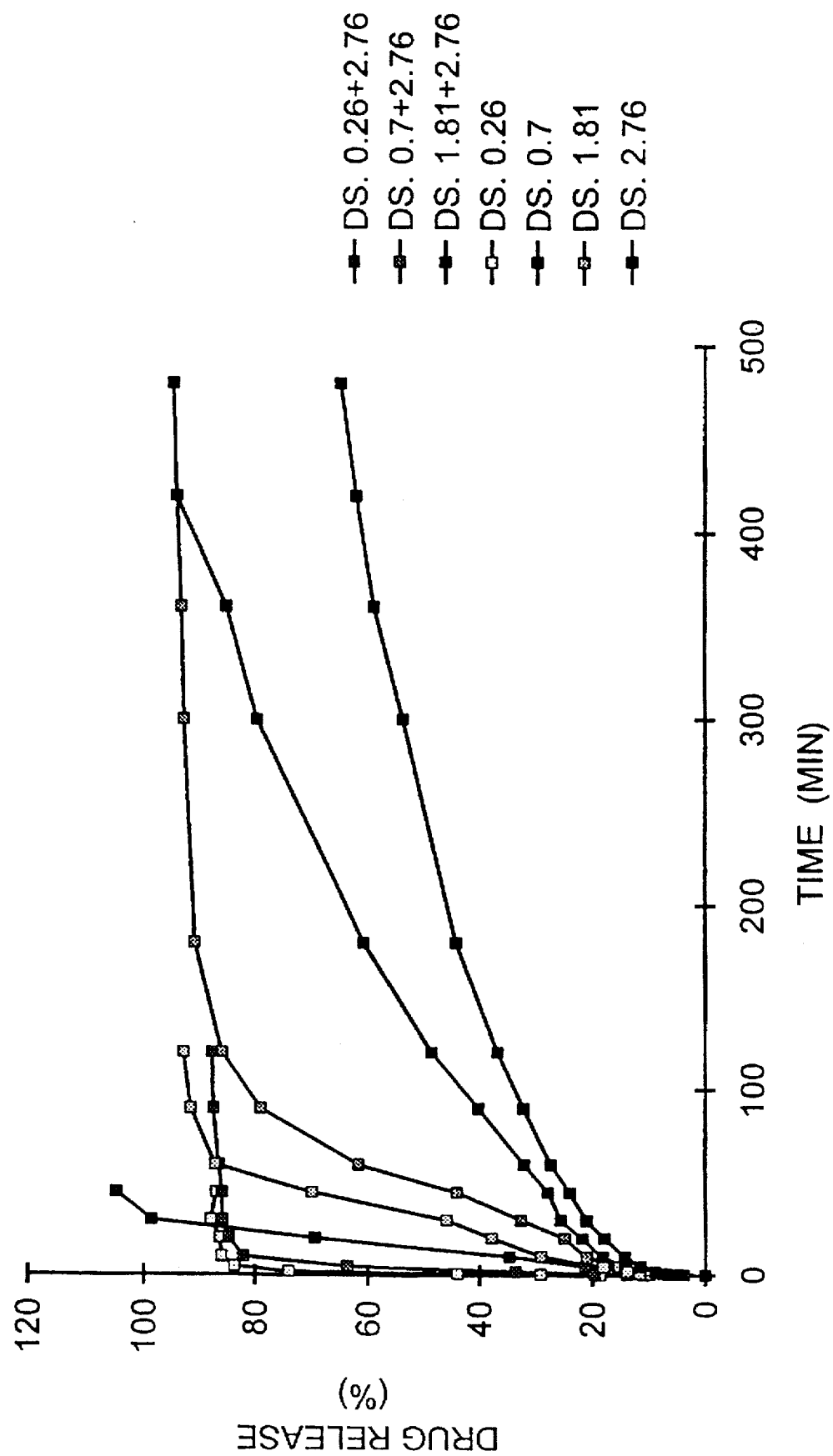
FIG. 10 depicts the drug release in percents as a function of time for starch acetate tablets. In the tablets starch acetate with one substitution degree or the 1:1 mixture two starch acetates with different substitution degrees have been used.

Drug release from a starch acetate matrix was delayed as starch acetate with high degree of substitution, ie. 2.76, was added (FIG. 10). The delay is particularly considerable as the degree of substitution of the other component of polymeric mixture is not less than 0.7. Tablet matrix containing starch acetate with high degree of substitution is mechanically strong, which sustains drug release. The release rate of active substance is the slowest as tablet matrix was composed using starch acetate with high degree of substitution (ds. 2.76) only (FIG. 10).

The breaking strength and disintegration time increased with increasing degree of substitution of the other component of polymer mixture (Table 4). The breaking strength values of tablets formed of mixtures either a) or b) are substantially identical, ie. 97N. The compression force was somewhat lower while tablets of mixture b) were produced. The value of breaking strength of these particular tablets could be greater if the compression force was the same as in the case of mixture a) tablets. The disintegration time was longer than two hours for each formulation. The macrostructure of a matrix prepared using either mixture b) or c) were undamaged after two hours, when the procedure was finished. In two hours mixture a) tablets were broken down in pieces and there were some pieces left in the glass cylinders of apparatus as the experiment came to an end.

Thus, it is possible to attain appropriate release profile mixing starch acetate powders with different degree of substitution.

EXAMPLE 11

The effect of origin of starch acetate on dissolution properties

Starch acetate used in previous experiments was processed from acid hydrolysed barley starch (HHOHRA). In this example starch acetate was processed from native barley starch and the degree of substitution of polymer was 1.76. The concentration of active substance, ie. propranolol hydrochloride, was 25% w/w. Tablets were prepared and tested using similar methods as previously.

Figure 11:
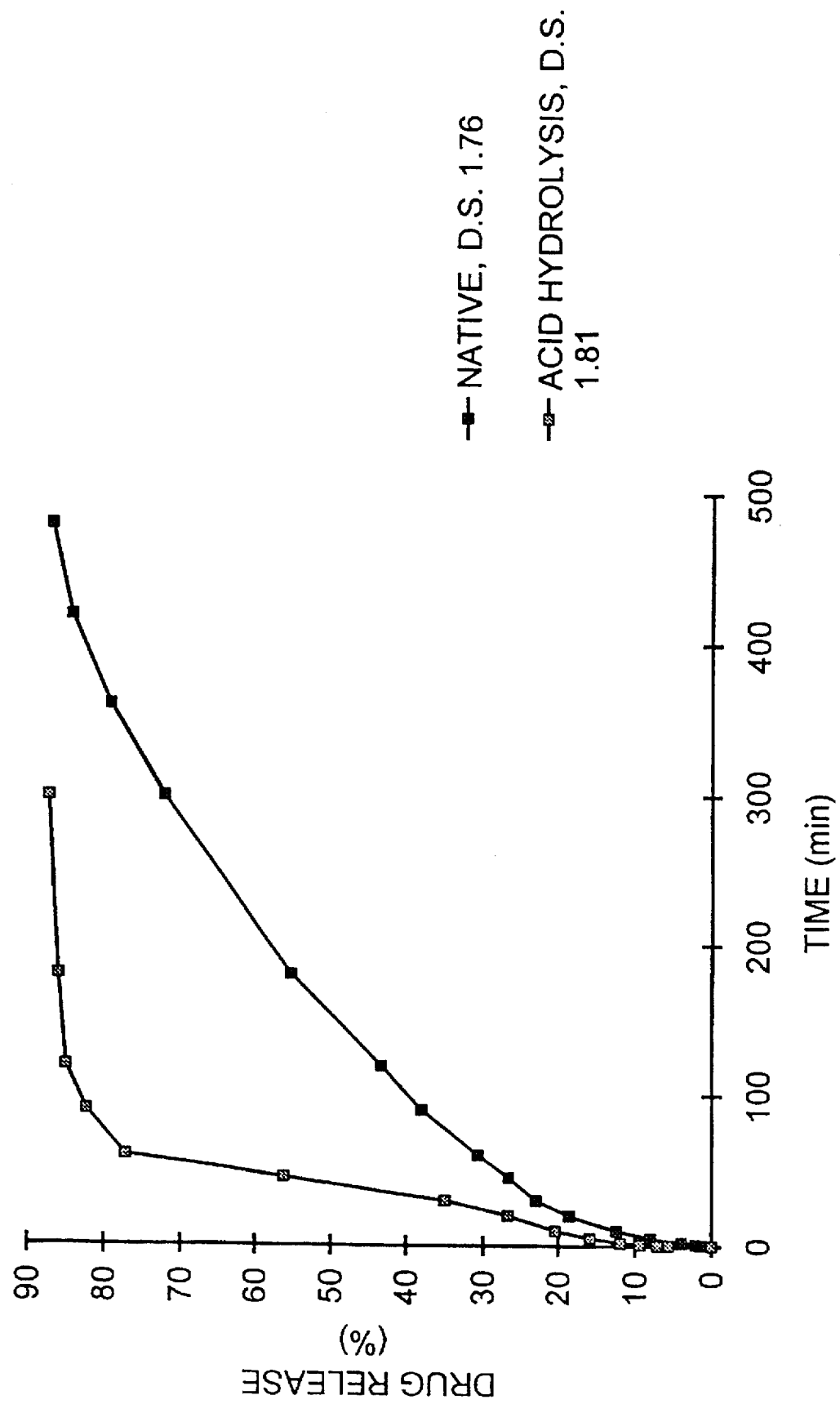
FIG. 11 depicts drug release in percents as a function of time for starch acetate tablets. As starting material for the starch acetate either native starch (native, D.S. 1,76) or acid hydrolysed barley starch (acid hydrolysis, D.S. 1.81) was used.

The rate of drug release is slower from a matrix containing native starch derivative than a matrix composed of acid thinned starch derivative (FIG. 11). The difference in release properties of two dissimilar kinds of matrix was remarkable, particularly after the first hour of experiment. Tablets containing starch acetate (DS. 1.81), processed from acid hydrolysed starch, disintegrated during the first hour of test and drug contents released completely. Particle size of native starch derivative seem to be markedly smaller than particle size of the other derivative. Native starch derivative formed mechanically though tablets, which might be the effect of small particle size. The disintegration time of these particular type of tablets was long. The release of drug is slow, because of relatively firm structure of matrix. The penetration of dissolution medium, which dissolves dispersed drug substance, into firm structure is slower and release of drug delays.

Thus, the grade of starch used to process starch acetate affects compression and controlled release properties of starch acetate.

EXAMPLE 12

The effect of pH of dissolution medium on drug release from starch acetate matrix Starch acetate tablets with the degree of substitution 1.81 were compressed and examined using identical procedures as formerly. The drug and excipient contents of tablet was also identical with earlier experiments. The dissolution tests were performed using dissolution medium with pH value of 2, 7 or 8.

Figure 12:
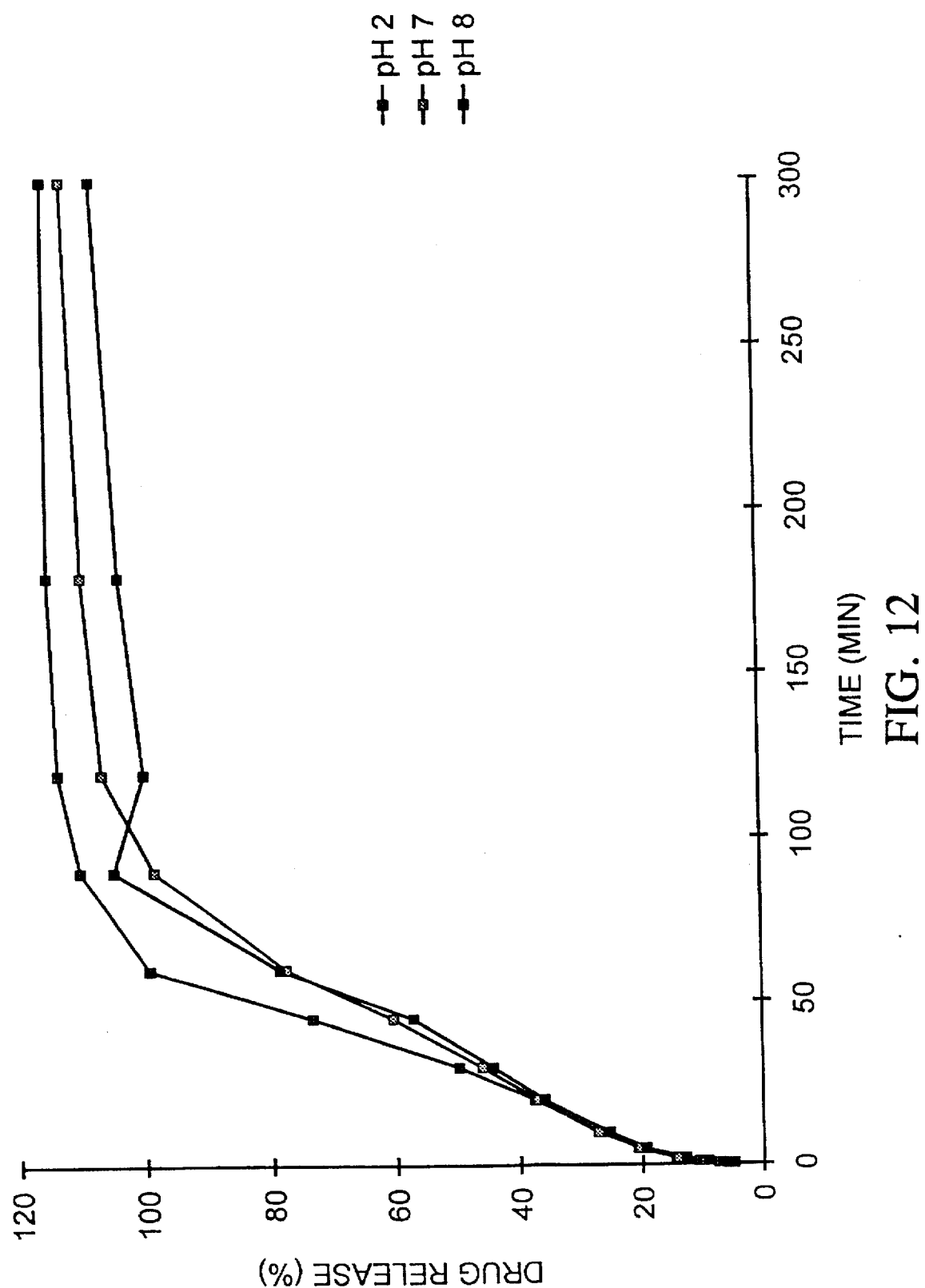
FIG. 12 depicts drug release in percents as a function of time for tablets of starch acetate. The pH of the disintegration medium was 2, 7 or 8.

Thus, the rate of drug release from starch acetate tablets is independent of pH value of dissolution medium (FIG. 12).

EXAMPLE 13

The effect of compression force on drug release properties of starch acetate

Figure 13:
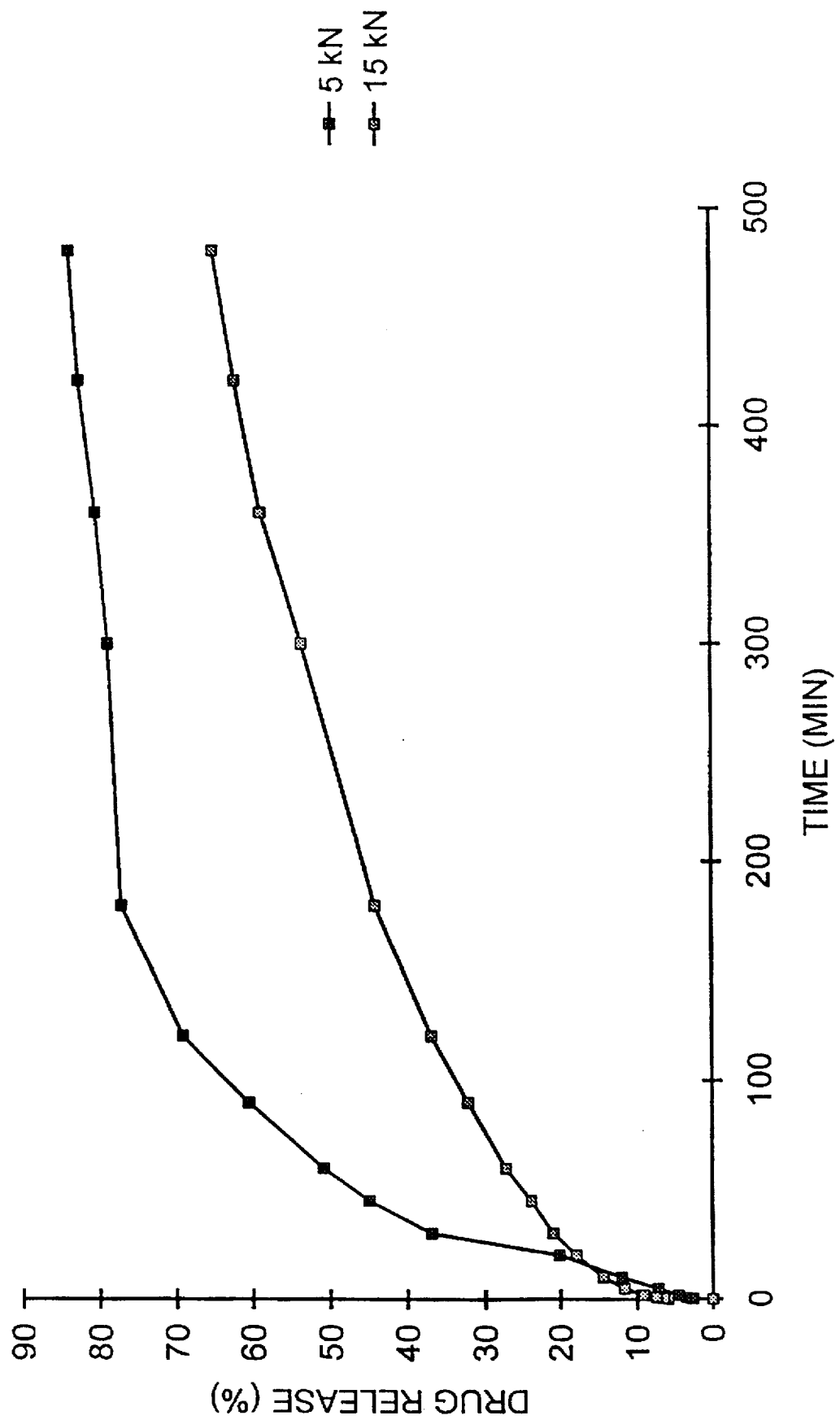
FIG. 13 depicts the drug release in percents as a function of time for tablets of starch acetate (substitution degree 2.76). Compression force of tablets was 5 or 15 kN.

In Example 7 two different compression force were used to press starch acetate tablets with degree of substitution 1.81. The effect of compression force on drug release properties of starch acetate was also studied using highly substituted derivative (DS. 2.76). The compression force was adjusted to 5 kN and result of dissolution test was competed to particular experiment, where tablets were compressed at 15 kN force. The release profiles of propranolol hydrochloride are shown in FIG. 13. Drug release was delayed with increasing compression force. Regardless of compression force amount of released drug substance is almost equal in the beginning of experiment, when drug particles on the surface of tablet begin to dissolve. As the compression force rises the structure of the polymer matrix becomes more dense and penetration of dissolving medium into centre parts of tablet slows down and rate of release diminishes.

Thus, it is possible to control drug release from starch acetate polymer matrix using polymer with particular degree of substitution and particular magnitude of compression force in tableting.

We claim:

1. A composition with modifiable excipient properties, comprising a compact, which in addition to at least one active ingredient comprises starch acetate, wherein the excipient properties of said composition are modifiable to be compatible with the intended excipient purpose by varying the substitution degree of starch acetate between 0.2–3.0, preferably 0.7–3.0 or/and changing the compressional force used in the manufacturing of the compact respectively.

2. The composition of claim 1, wherein the number average polar mass (Mn) for the starch used in the production of the starch acetate is about 10 000–250 000 g/mol.

3. The composition of claim 1, wherein the amount of starch acetate is about 10–99% (w/w).

4. The composition of claim 1, which comprises a compact for controlled release of the active ingredient in which compact the substitution degree of the starch acetate is about 0.7–3.0.

5. The composition of claim 4, wherein the amount of starch acetate is above 50% (w/w).

6. The composition of claim 1, which comprises a compact for controlled release of at least one active ingredient, which compact comprises at least two starch acetates with different substitution degrees.

7. The composition of claim 1, which is a compact for controlled release of an active ingredient, the amount of which is about 0.001–50% (w/w).

8. The composition of claim 1, comprising a compact in which starch acetate is the only excipient, which functions as a disintegrant, filler, binder and an agent which regulates the controlled release of the active ingredient.

9. The composition of claim 1, which is a compact obtainable by adjusting the substitution degree of starch acetate and changing the compressional force gives the release profiles according to FIGS. 6–13.

10. The composition of claim 1, wherein the starch acetate is prepared from native or hydrolysed starch.

11. The composition of claim 10, wherein the starch acetate is barley or oats starch acetate.

12. The composition of claim 8, wherein the starch acetate functions as a disintegrant or filler when the substitution degree is 0.2 to 0.7.

13. The composition of claim 8, wherein the starch acetate functions as a binder when the substitution degree is about 0.2–3.

14. The composition of claim 8, wherein the starch acetate functions as a modifier of the controlled release of the active ingredient when the substitution degree is above about 0.7.

15. A method for the preparation of a composition with modifiable properties, comprising the steps of mixing at least one active ingredient with starch acetate, the substitution degree of which is about 0.2–3.0 and compressing said mixture with such a force that a compact with properties compatible with the intended use are obtained.

16. The method of claim 15, wherein the starch used for producing starch acetate has an number average molar mass (Mn) which is about 10 000–25 000 g/mol.

17. The method of claim 15, wherein the amount of starch acetate is about 10–99% (w/w).

18. The method of claim 15, wherein the active ingredient and the starch acetate having a substitution degree of about 0.2–3.0 are mixed and the mixture compressed with a force sufficient to provide a compact useful for the controlled release of the active ingredient.

19. The method of claim 18, wherein the amount of starch acetate is more than about 50% (w/w).

20. The method of claim 15, wherein at least one active ingredient and at least two starch acetates with different substitution degrees are mixed and compressed to obtain a compact from which the release of the active ingredient can be more exactly controlled.

21. The method of claim 15, wherein by varying the amount of the active ingredient between about 0.5–50% (w/w) a compact is obtained, from which the controlled release of the active ingredient is can be more exactly controlled.

22. The method of claim 15, wherein the starch acetate is essentially the only excipient, which functions as a disintegrant, filler, binder and modifier of the controlled release of the active ingredient and by the aid of which it is possible to essentially eliminate the use of conventional disintegrant, fillers and binders.

23. The method of claim 15, wherein by mixing and compressing the active ingredient and starch acetate a compact is obtained, from which the active ingredient is released according to the profile in FIGS. 6 and 13.

24. The method of claim 15, wherein the starch acetate is produced from native or acid hydrolysed starch.

25. The method of claim 24, wherein the starch acetate is prepared from barley or oats starch.

26. The method of claim 22, wherein a compact useful as a disintegrant or filler is prepared by mixing an active ingredient and starch acetate having a substitution degree of 0.2 to about 0.7 and compressing with the appropriate force.

27. The method of claim 22, wherein a compact useful as a binder is prepared by mixing the active ingredient and starch acetate having a substitution degree of about 0.2–3 and compressing with the appropriate force.

28. The method of claim 22, wherein a compact useful for the controlled release of the active ingredient is prepared by mixing the active ingredient and starch acetate having a substitution degree of more than about 0.7 and compressing with the appropriate force.

29. The method of claim 16, wherein the controlled release of the active ingredient is controlled by mixing it with starch acetates having different degrees of substitution.

30. The method of claim 22, wherein the controlled release of the active ingredient can be regulated by varying the relative proportion of the amount of active ingredient.

31. The method of claim 22, wherein the compact is produced from granulated or ungranulated powders by a method of direct compressing without granulation or compression after wet or dry granulation.

32. A method of using the composition of claim 1 for the production of pharmaceutical tablets comprising substances usefuls as medicines.

33. A method of using the composition of claim 1 for the preparation of granulates comprising fertilizers.

34. A method of using the composition of claim 1 for the preparation of herbicidal preparates.

35. A method of using the composition of claim 1 for the preparation of products comprising reagents for diagnostic.

36. A composition with modifiable excipient properties, comprising at least one active ingredient and an excipient consisting essentially of starch acetate having a substitution degree of starch between 0.2 and 3.0.

37. A composition according to claim 36 in compacted form.

38. A composition according to claim 36 wherein the amount of starch acetate is about 10–99% (w/w) and the number average molecular mass (Mn) for starch used in the production of the starch acetate is about 10,000–250,000 g/mol.

39. A composition according to claim 36 wherein said modifiable excipient properties comprise the properties of sustained release rate profiles, constant rate profiles or gradually sustaining and subsequently accelerating drug release profiles, and wherein said starch acetate functions as a disintegrant, filler, binder and an agent which regulates the controlled release of the active ingredient.

40. The composition of claim 1, which is a compact obtainable by adjusting the substitution degree of starch acetate and changing the compressional force and which gives release profiles, wherein the release of active ingredient is modifiable from relatively rapid release, which decreases gradually or dramatically until significant delayed release is achieved, by modifying essentially 5 variables, said variables being the degree of substitution compressional force, amount of active ingredient and type as well as particle size of the starch acetate in such a way that the more significant delayed release is achieved with a higher degree of substitution, higher pressures, and smaller amount of active ingredient and particle size of the starch acetate, the release rate being essentially independent of the pH value of the dissolution medium, the degree of release rate being further modifiable by using mixtures of starches with different particle sizes and substitution degrees.

41. The method of claim 15, wherein by mixing and compressing the active ingredient and starch acetate a compact, wherefrom the release of active ingredient is modifiable from relatively rapid release, which decreases gradually or dramatically until significant delayed release is achieved and which is obtainable mainly by mixing starch acetate with different substitution degree and different amounts of active ingredient and by using different compressional forces to said mixture and additionally modifying the type as well as particle size of the starch derivative in such a way that the more significant delayed release is achieved with the higher degree of substitution, the higher pressures and smaller amount of active ingredient and particle size of the starch derivative, the release rate being essentially independent of the pH value of the dissolution medium, the degree of release rate being further modifiable in a desired way by using mixtures of starches with different particle sizes and substitution degrees.

42. A composition according to claim 1, wherein the number average molecular mass (Mn) for the starch used in the production of the starch acetate is about 50,000–220,000 g/mol.

43. A composition according to claim 1, wherein the amount of starch acetate is 15–90% (w/w).

44. A composition according to claim 4, wherein the number average molecular mass (Mn) for the starch used in the production of the starch acetate is about 50,000–220,000 g/mol, and the amount of starch acetate is about 15–90% (w/w).

45. The composition of claim 1, which is a compact for controlled release of an active ingredient, the amount of which is about 0.01–25% (w/w).

46. The composition of claim 8, wherein the starch acetate functions as a modifier of the controlled release of the active ingredient when the substitution degree is above about 1.5.

47. The method of claim 15, wherein the starch used for producing starch acetate has a number average molar mass (Mn) which is about 50,000–220,000 g/mol.

48. The method of claim 15, wherein the amount of starch acetate is about 15–90% (w/w).

49. The method of claim 15, wherein by varying the amount of the active ingredient about 1.0–25% (w/w) a compact is obtained, from which the controlled release of the active ingredient can be more exactly controlled.

50. The method of claim 22, wherein a compact useful as a binder is prepared by mixing the active ingredient and starch acetate having a substitution degree of about 0.7–3.0 and compressing with the appropriate force.

51. The method of claim 22, wherein a compact useful for the controlled release of the active ingredient is prepared by mixing the active ingredient and starch acetate having a substitution degree of more than about 1.5 and compressing with the appropriate force.

* * * * *